United States Patent

Asher et al.

Patent Number: 5,257,993
Date of Patent: Nov. 2, 1993

[54] TOP-ENTRY ROD RETAINER

[75] Inventors: Marc A. Asher, Prairie Village, Kans.; Robert W. Gaines, Jr., Columbia, Mo.; Walter E. Stripgen, Golden, Colo.; Frank S. Janson, Rocky River, Ohio; William L. Carson, Columbia, Mo.; Terrence M. Stahurski, Rocky River, Ohio; Charles F. Heinig, Ware Neck, Va.

[73] Assignee: AcroMed Corporation, Cleveland, Ohio

[21] Appl. No.: 771,723

[22] Filed: Oct. 4, 1991

[51] Int. Cl.⁵ .............................. A61F 5/04
[52] U.S. Cl. ........................ 606/61; 606/72
[58] Field of Search .......... 606/61, 62, 72, 73

[56] References Cited

U.S. PATENT DOCUMENTS

| | | | |
|---|---|---|---|
| 4,269,178 | 5/1981 | Keene | 606/61 |
| 4,433,676 | 2/1984 | Bobechko | 606/61 |
| 4,815,453 | 3/1989 | Cotrel | 606/61 |
| 4,887,596 | 12/1989 | Sherman | 606/73 X |
| 4,950,269 | 8/1990 | Gaines, Jr. | 606/61 |
| 5,010,879 | 4/1991 | Moriya et al. | 606/61 X |
| 5,024,213 | 6/1991 | Asher et al. | 606/61 X |
| 5,074,864 | 12/1991 | Cozad et al. | 606/61 X |
| 5,102,412 | 4/1992 | Rogozinski | 606/61 |
| 5,147,360 | 9/1992 | Dubousset | 606/61 |

FOREIGN PATENT DOCUMENTS 3032237   3/1982   Fed. Rep. of Germany ........ 606/61

Primary Examiner—Robert Bahr
Assistant Examiner—Linda C. M. Dvorak
Attorney, Agent, or Firm—Tarolli, Sundheim & Covell

[57] ABSTRACT

An apparatus for use in retaining a longitudinally extending member in position relative to a spinal column includes a top-entry hook assembly having a hook portion which is engageable with a spinal column. A body extending upwardly from the hook portion and has an open ended recess which extends through the body and is open along one side to enable a rod or longitudinal member to be moved into the recess through the open side. An end cap is engageable with the body to close the upper side opening. A clamp member or set screw is disposed at the center of the end cap to clamp the rod in the recess in the body. The end cap and body are interconnectable by different types of connectors including a bayonet connector, a linear cam connector, or a threaded connector.

5 Claims, 8 Drawing Sheets

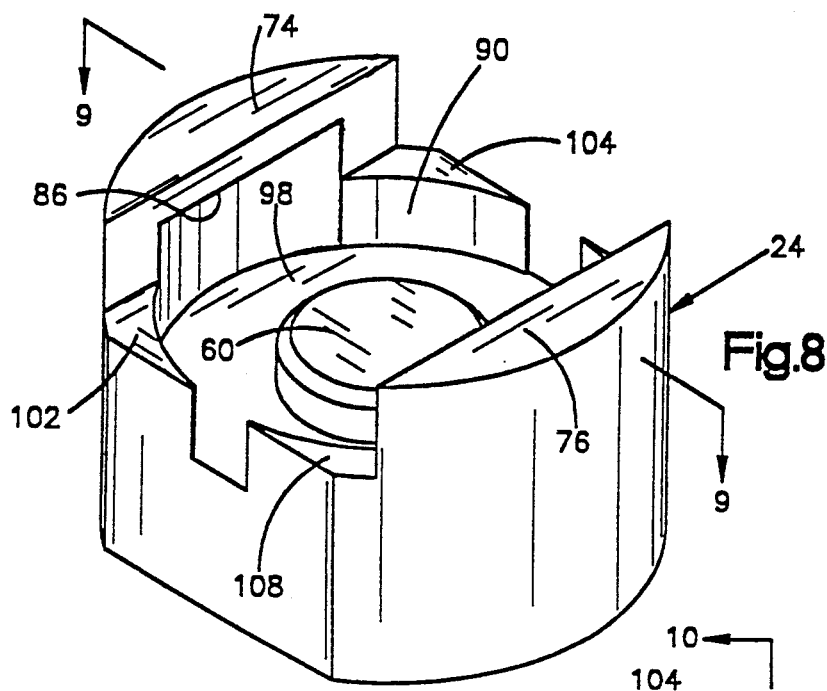
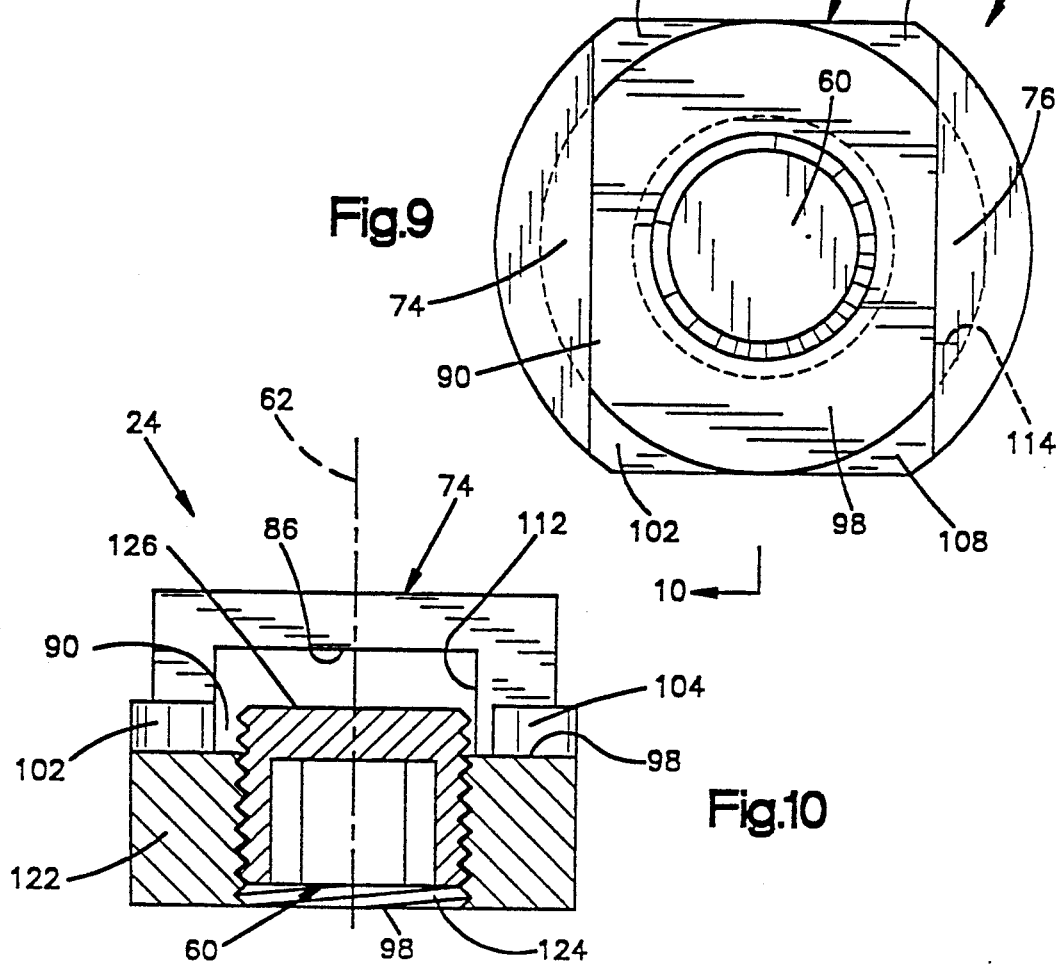

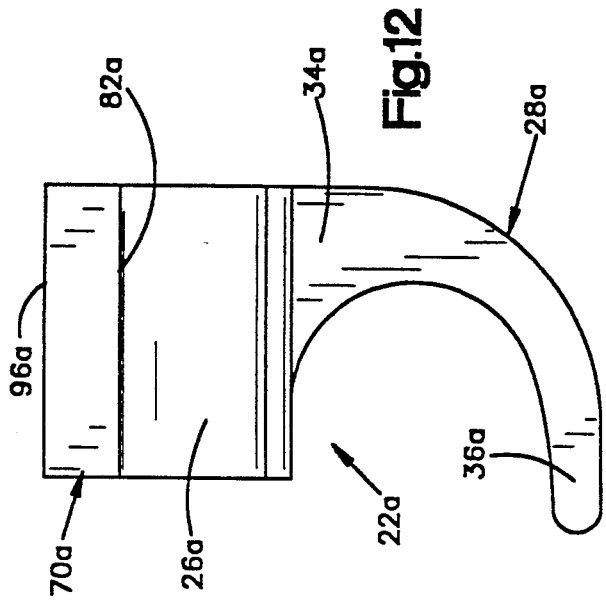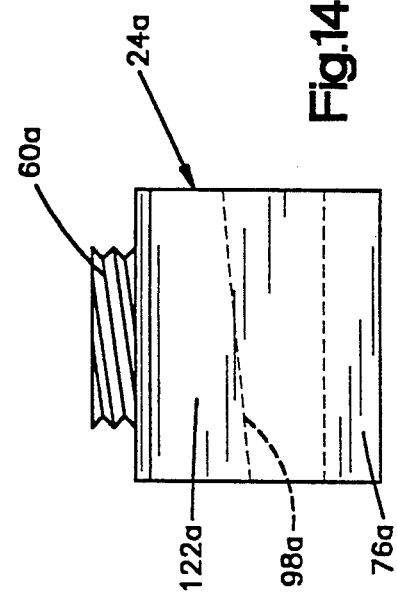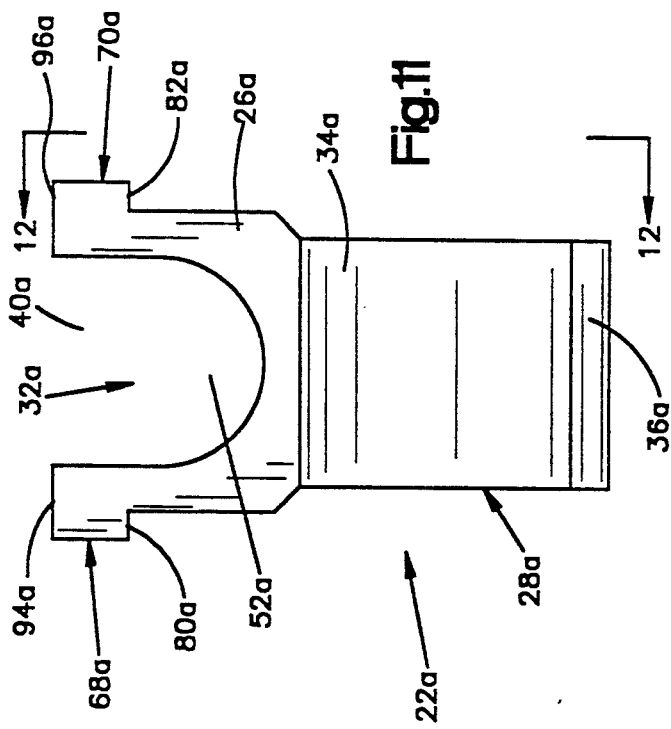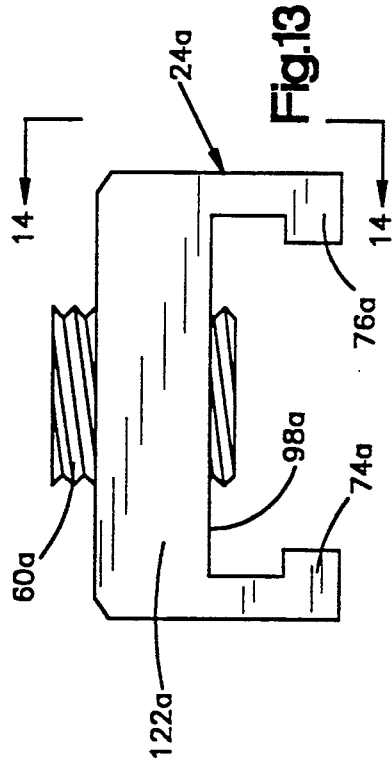

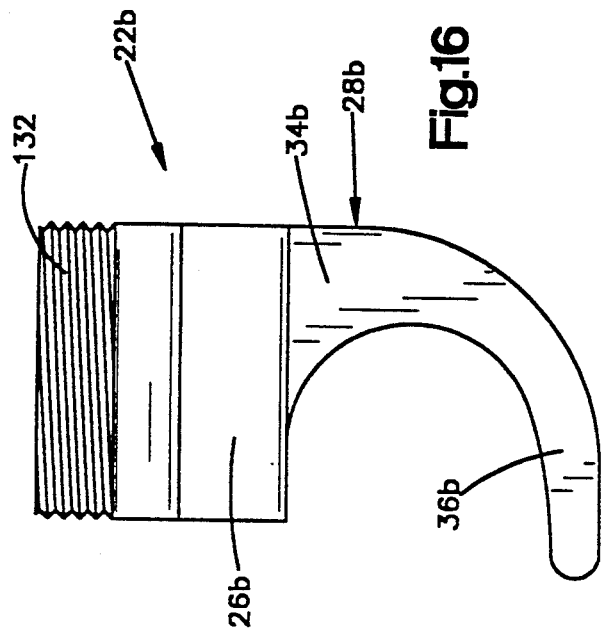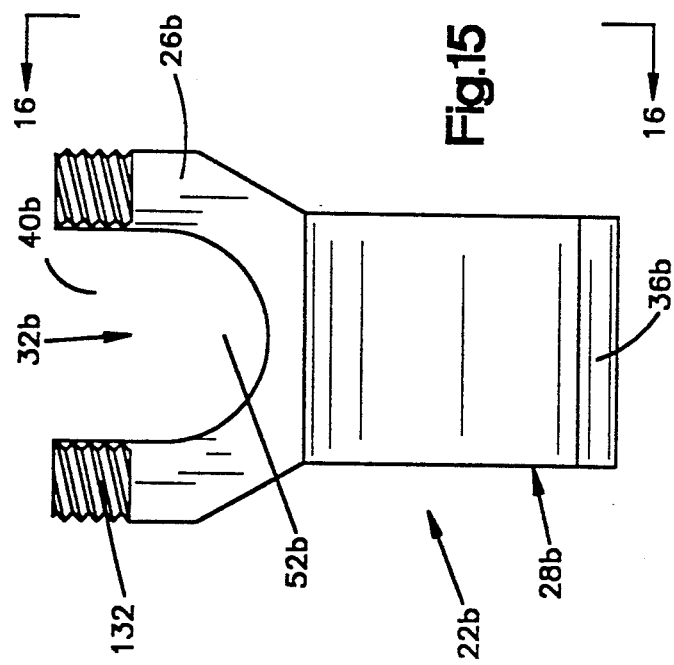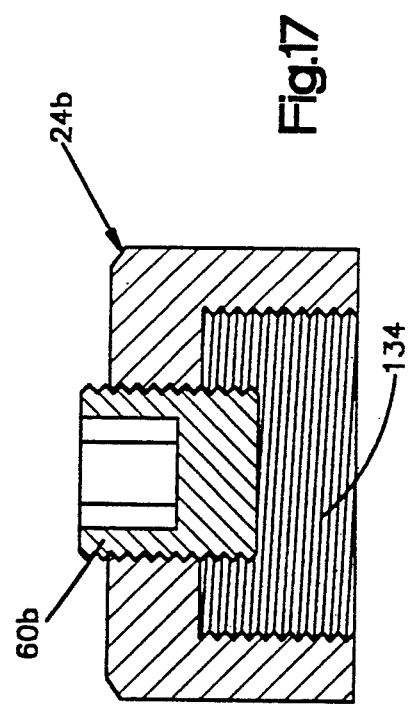

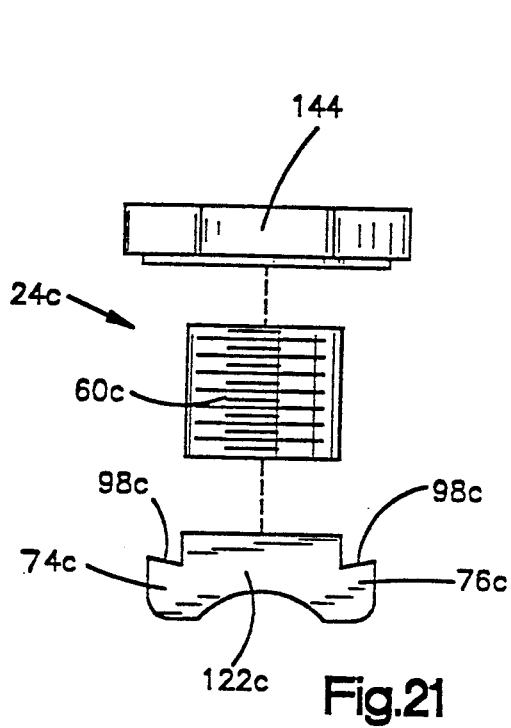
Fig.21
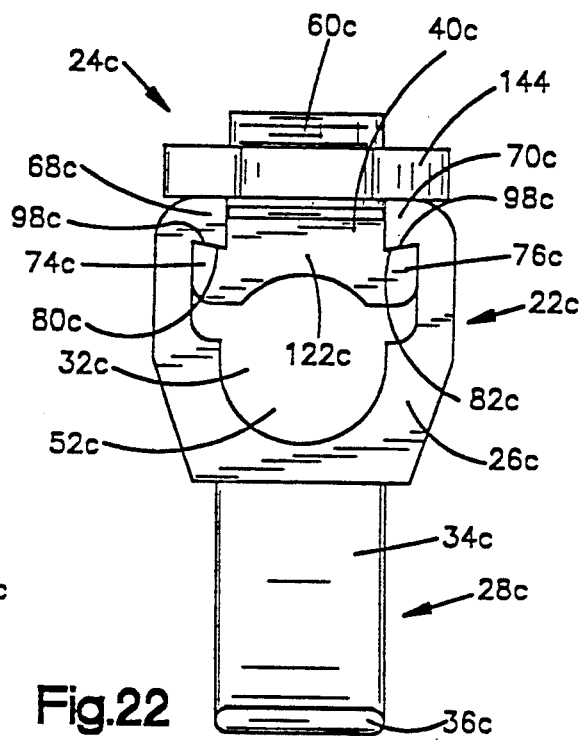
Fig.22
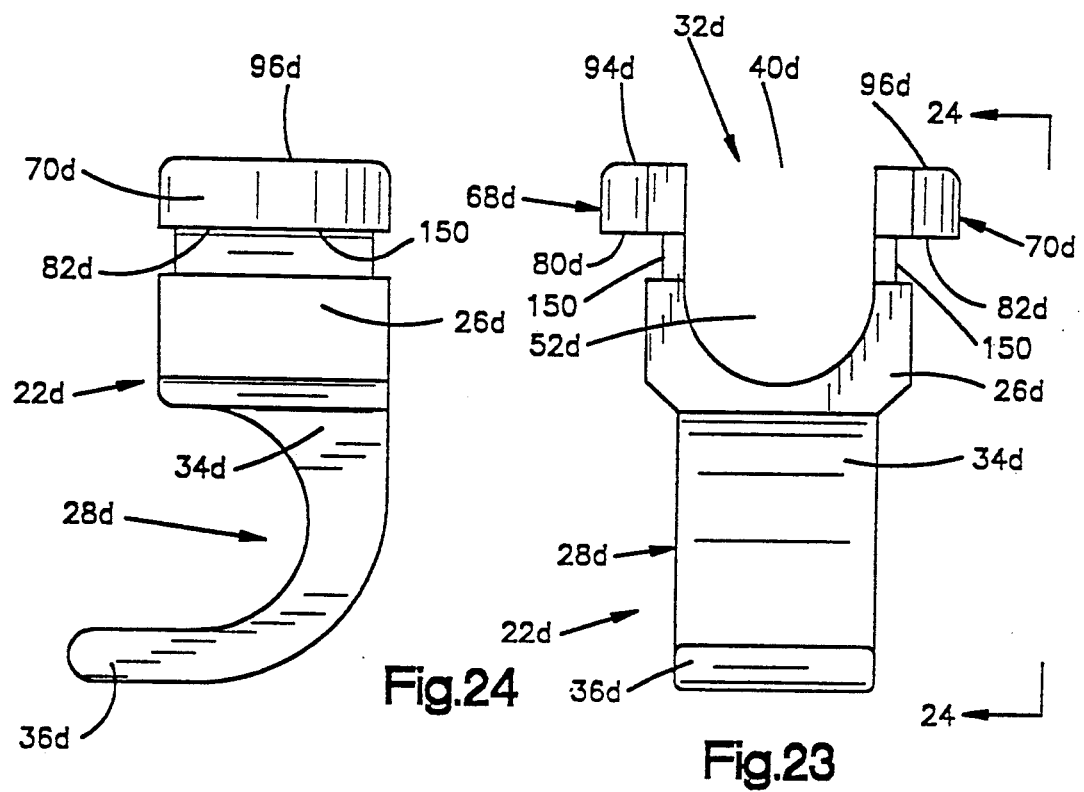
Fig.24
Fig.23

TOP-ENTRY ROD RETAINER

BACKGROUND OF THE INVENTION

The present invention relates to an implant which engages a spinal column to hold a longitudinal member or rod in position relative to the spinal column.

Spinal implants have been used in treatment of patients with deformed and/or mechanically insufficient spinal columns. Longitudinal members or rods have been contoured to a desired configuration and connected with a spinal column. Among the various devices used to connect a rod with a spinal column have been hooks having through openings which receive the rod. While the hook is loose on the rod, a blade or free end of the hook is moved into engagement with the spinal column. Once the hook has been positioned relative to the spinal column, a set screw or clamp member is tightened to securely interconnect the hook and the rod.

In the past, difficulties have been encountered in positioning the hook and rod relative to the spinal column. If the hook is placed on the rod before being connected with the spinal column, the rod tends to interfere with placement of the hook relative to the spinal column. If the hook is connected with the spinal column before being positioned on the rod, difficulty may be encountered in moving the rod through an opening in the hook without disturbing the placement of the hook relative to the spinal column.

The concept of providing a top-entry opening in a hook to receive a rod without sliding the hook along the rod is disclosed in U.S. Pat. No. 4,269,178 issued May 26, 1981 and entitled "Hook Assembly For Engaging A Spinal Column". This patent teaches that the hook is to be held in place by the use of a sleeve and a locking nut. The locking nut engages external threads on the rod and must be threaded along the rod to a position where the hook is to be located. In addition, the sleeve must be positioned on the rod adjacent to the locking nut

SUMMARY OF THE INVENTION

The present invention provides an apparatus for use in retaining a longitudinally extending member in position relative to a spinal column. The apparatus includes a top-entry hook assembly which can be positioned relative to a longitudinal member or rod without moving the hook assembly along the rod and/or moving another article, such as a locknut or sleeve, along the rod. The hook assembly includes a body having an open ended recess which extends through the body and is open at both ends and along one side to enable the rod to be moved into the recess. A hook extends from a side of the body opposite from the side opening through which the rod is inserted into the recess. The hook is engageable with a spinal column. Once the hook has engaged the spinal column and the rod has been inserted into the recess, an end cap is connected with the body to block the side opening through which the rod was moved into the recess. A clamp member is disposed in the center of the end cap to clamp the rod against the bottom of the recess in the body.

One embodiment of the end cap includes a bayonet connector which is readily engaged under adverse conditions which may be encountered during an implant procedure. The bayonet connector includes flanges disposed on an upper end of the body and mating flanges disposed on the end cap. When the end cap and body are to be interconnected, the end cap is telescoped over the flanges o the body and then rotated to engage the flanges on the body with the flanges on the end cap.

Another connector for interconnecting the end cap and body includes linear flanges on the body which engage linear flanges on the end cap. The linear flanges on either the body or end cap have cam surfaces which interact with other flange surfaces to hold the end cap in place. In another embodiment of the top-entry hook assembly, the body is provided with an external thread convolution which is engaged by an internal thread convolution on the end cap.

In another embodiment of the top-entry hook assembly the end cap is internal to the recess. Linear flanges on the end cap engage linear flanges on the body. A lock nut and set screw hold the end cap in position relative to the body.

In another embodiment of the top-entry hook assembly the end cap is provided with an alternative bayonet connector. Flanges disposed on an upper end of the body mate with flanges disposed on the end cap. The flanges on the end cap extend into a groove formed in the body just below the flanges on the body. When the end cap and the body are to be interconnected, the end cap is telescoped over the flanges on the body and rotated to engage the flanges on the body with the flanges on the end cap.

BRIEF DESCRIPTION OF THE DRAWINGS

The foregoing and other features of the invention will become more apparent upon a consideration of the following description taken in connection with the accompanying drawings, wherein:

FIG. 8 is a pictorial illustration of an end cap of the top entry hook assembly of FIG. 1, the lower side of the end cap facing upwardly to expose a pair of connector flanges;

FIG. 9 is a bottom plan view, taken generally along the line 9—9 of FIG. 8, illustrating the relationship of a clamp member or set screw to the flanges on the end cap;

FIG. 10 is a sectional view, taken generally along the line 10—10 of FIG. 9, further illustrating the construction of the end cap;

FIG. 11 is a front elevational view, generally similar to FIG. 5, of a hook portion of a second embodiment of the top-entry hook assembly;

FIG. 12 is a side elevational view, taken generally along the line 12—12 of FIG. 11, further illustrating the construction of a hook portion of the top-entry assembly;

FIG. 13 is a front elevational view of an end cap which is connected with the hook portion of FIG. 11 to close an opening in the upper side of a recess in the top-entry hook assembly;

FIG. 14 is a side elevational view, taken generally along the line 14—14 of FIG. 13, further illustrating the construction of the end cap;

FIG. 15 is a front elevational view, generally similar to FIG. 5, of an externally threaded hook portion of a third embodiment of the top-entry hook assembly;

FIG. 16 is a side elevational view, taken generally along the line 16—16 of FIG. 15 further illustrating the construction of the hook portion of the top-entry hook assembly; and FIG. 17 is a sectional view of an internally threaded end cap used with the hook portion of FIGS. 15 and 16;

FIG. 21 is an exploded view of an end cap which is connected with the hook portion of FIG. 20;

FIG. 22 is a front elevational view showing the end cap of FIG. 21 connected with the hook portion of FIG. 20;

FIG. 23 is a front elevational view, generally similar to FIG. 5, of a hook portion of a sixth embodiment of the top-entry hook assembly;

FIG. 24 is a side elevational view, taken generally along the line 24—24 of FIG. 23, further illustrating the construction of a hook portion of the top-entry hook assembly;

DESCRIPTION OF SPECIFIC PREFERRED EMBODIMENTS OF THE INVENTION

General Description

Figure 1:
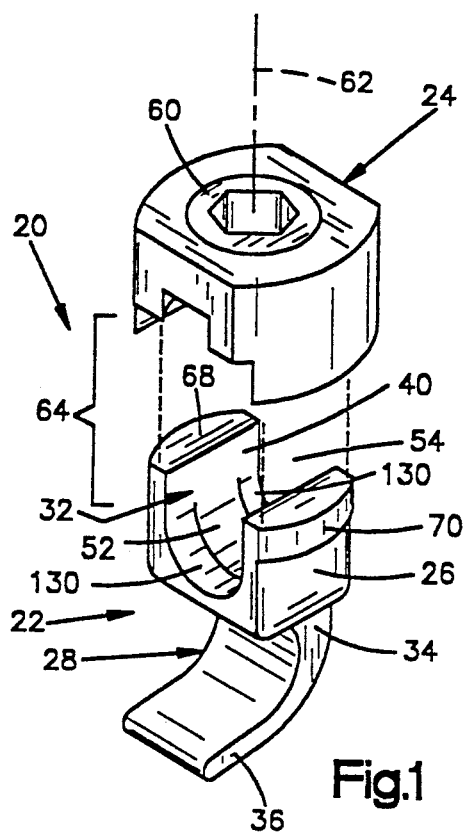
FIG. 1 is an exploded illustration of a top-entry hook assembly constructed in accordance with the present invention; 25

A top-entry hook assembly 20 constructed in accordance with the present invention is illustrated in FIG. 1. The top-entry hook assembly 20 includes a one-piece, metal, hook portion 22 and a metal end cap 24. The hook portion 22 includes a generally rectangular body 26 and a downwardly extending hook 28.

The body 26 of the hook portion 22 has an open ended recess 32 which extends through the body and is open at opposite ends of the body to receive a rod or longitudinal member. The hook 28 includes a shank portion 34 and free end or blade portion 36 which are engageable with an element of a spinal column to interconnect the spinal column and a rod extending through the open ended recess 32.

Figure 7:
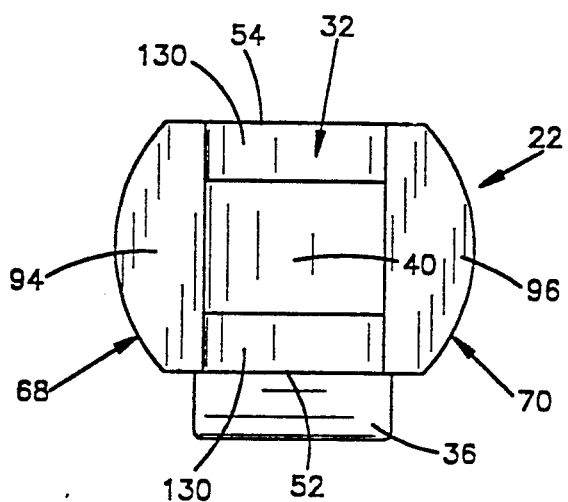
FIG. 7 is a top plan view, taken generally along the line 7—7 of FIG. 5, illustrating the configuration of a side opening through which a longitudinal member or rod is inserted into a recess in the body portion of the top-entry hook assembly.

The recess 32 has a first larger radius R1 (FIG. 5) and a second smaller radius R2. The radius R2 forms a pair of axially spaced arcuate surfaces 130 (FIG. 7). The pair of axially spaced arcuate surfaces 130 engage portions of the rod at axially spaced locations. Reference is hereby made to U.S. Pat. No. 5,024,213 to Asher et al. and assigned to the same assignee as the present invention. U.S. Pat. No. 5,024,213 describes the arcuate surfaces and their function in greater detail.

In accordance with one of the features of the present invention, the end cap 24 (FIG. 1) is removable from the hook portion 22. When the end cap 24 is removed from the hook portion 22, a rectangular upper side opening 40 to the recess 32 is exposed. A rod or other longitudinal member can be readily inserted through the upper side opening 40 into the recess 32.

Figure 2:
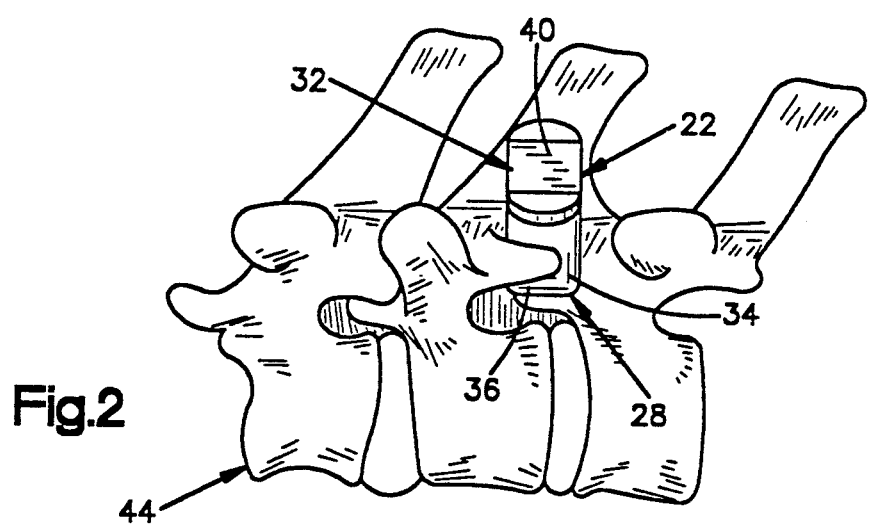
FIG. 2 is a pictorial illustration depicting the manner in which a hook portion of the top-entry hook assembly of FIG. 1 is positioned relative to a spinal column, an end cap of the hook assembly having been removed.

The hook portion 22 may be mounted on a spinal column 44 by interlaminar placement of the hook 28 as shown in FIG. 2. However, the hook 28 could also have supralaminar, infratransverse or supratransverse placement relative to the spinal column 44 if desired.

Figure 3:
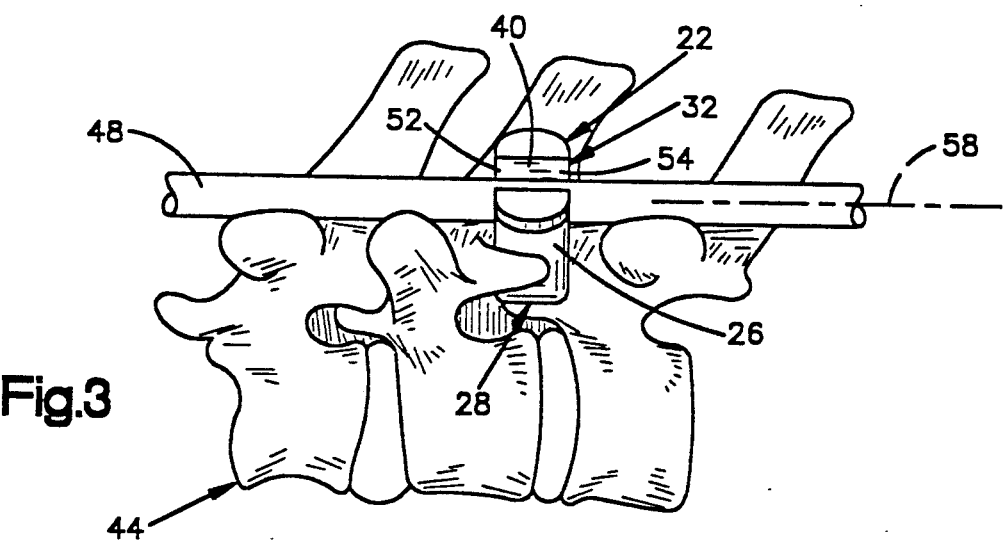
FIG. 3 is an illustration, generally similar to FIG. 2, depicting the manner in which a longitudinal member or rod is placed in a recess in the hook portion after the hook portion has been positioned relative to the spinal column.
Figure 4:
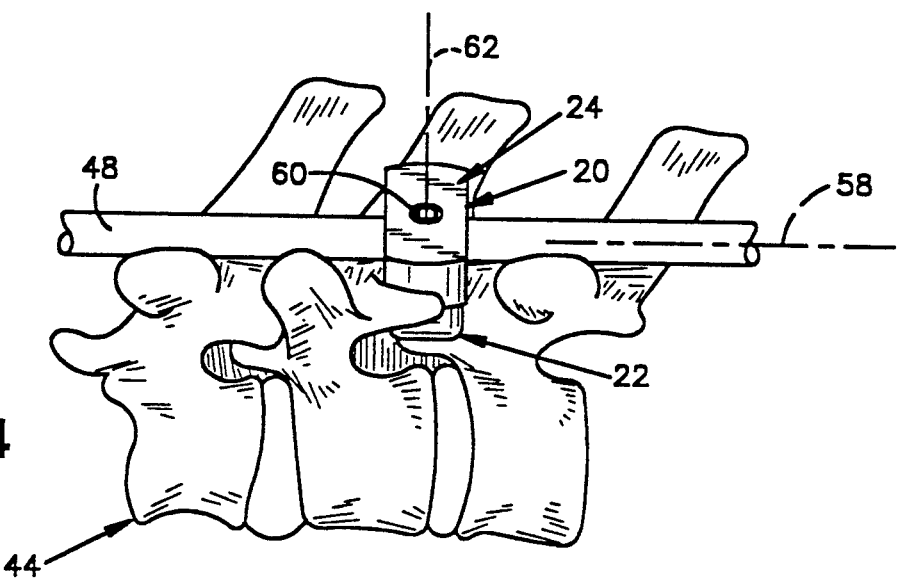
FIG. 4 is an illustration, generally similar to FIG. 3, of the top entry hook assembly with the end cap in place.

Once the hook portion 22 of the hook assembly 20 has been connected with the spinal column 44 as shown in FIG. 2, a rod or longitudinal member 48 may be placed in the recess 32 (FIG. 3). The cylindrical rod 48 is placed in the recess 32 by moving the rod downwardly through the open upper side 40 of the recess. When the rod 48 has been positioned in the recess 32, the rod extends through generally U-shaped end openings 52 and 54 (FIGS. 1 and 3) disposed at opposite sides of the body 26. When the rod 48 is placed in the recess 32, a longitudinal central axis 58 of the rod extends generally parallel to the free end or blade portion 36 of the hook 28. The rod 48 is shown in FIGS. 3 and 4 as straight but would normally be curved to a desired configuration. If desired, devices other than the hook 28 may be used to connect the body 26 with the spinal column 44.

Once the rod 48 has been placed in the open ended recess 32, the end cap 24 is connected with the hook portion 22 (FIG. 4) The end cap 24 blocks the upper side opening 40 of the recess 22 while enabling the rod 48 to extend through the end openings 52 and 54 (FIG. 3) of the recess 32. Once the end cap 24 has been connected with the hook portion 22 of the hook assembly 20, a clamp member or set screw 60 (FIGS. 1 and 4) is tightened to interconnect the rod 48 and hook assembly. The recess 32 has a vertical dimension as viewed in FIG. 5 such that the rod 48 can be moved vertically in the recess prior to the set screw 60 being tightened.

The clamp member or set screw 60 is located at the center of the end cap 24. The set screw 60 has a vertical (as viewed in FIG. 1) central axis 62 which intersects the horizontal (as viewed in FIG. 4) longitudinal central axis 58 of the rod 48. The set screw 60 presses the rod 48 against the arcuate surfaces 130 to clamp the rod against movement relative to the hook assembly 20. In addition to pressing the rod 48 against the arcuate surfaces 130, the set screw 60 applies an upwardly directed force against the end cap 24 to retain the end cap against disengagement from the hook portion 22.

Since the end cap 24 is disengageable from the hook portion 22 of the hook assembly 20, the rod 48 can be readily inserted into the recess 32 through the upper side opening 40. This enables the rod 48 and hook assembly 20 to be positioned relative to each other without sliding the hook assembly along the rod or moving the rod axially through the hook assembly. By mounting the clamp member or set screw 60 in the end cap 24, it is not necessary to provide a clamp member which is separate from the hook assembly 20 and which must be positioned along the rod 48.

Hook Assembly—Bayonet Connector

In the embodiment of the hook assembly 20 illustrated in FIGS. 1 through 10, a bayonet connector 64 (FIG. 1) is used to interconnect the end cap 24 and hook portion 22 of the hook assembly 20. The bayonet connector 64 has components which are readily positioned relative to each other by a surgeon during an operation. The bayonet connector 64 is held in an engaged condition by force transmitted between the set screw 60 and the rod 48 when the top-entry hook assembly 20 is positioned relative to the spinal column 44 and connected with the rod.

The bayonet connector 64 includes a pair of flanges 68 and 70 (FIGS. 1, 5, 6 and 7) disposed at the upper end of the body 26. When the end cap 24 is connected with the hook portion 22, the flanges 68 and 70 are enclosed by the end cap and engage flanges 74 and 76 (FIGS. 8-10) formed on the end cap 24. When the end cap 24 is connected with the hook portion 22, flat bottom surfaces 80 and 82 on the hook portion flanges 68 and 70 engage flat inwardly facing surfaces on the flanges 74 and 76 on the end cap 24.

Thus, when the end cap 24 is connected with the hook portion 22, the flat lower side surface 80 on the hook flange 68 (FIG. 5) abuttingly engages a flat inner side surface 86 (FIGS. 8 and 10) on the end cap flange 74. Similarly, the flat lower side surface 82 on the hook flange 70 abuttingly engages a flat inner side surface (not shown) on the end cap flange 76. Abutting engagement between the flanges 68 and 70 on the hook portion 22 and the flanges 74 and 76 on the end cap 24 hold the end cap on the hook portion 22. The end cap 24 extends across the open upper side 40 (FIG. 5) of the recess 32 to close the recess.

After the rod 48 has been inserted through the open upper side 40 of the recess 32, the end cap 24 is connected with the hook portion 22. This is accomplished by positioning the end cap 24 in axial alignment with the hook portion 22 with the flanges 74 and 76 facing downwardly toward the flanges 68 and 70 on the hook portion 22. A transverse opening 90 (FIGS. 8 and 9) between the flanges 74 and 76 on the end cap 24 is aligned with the flanges 68 and 70 (FIG. 7) on the upper end of the hook portion 22. At this time, the flanges 68 and 70 on the hook portion 22 are offset by 90° from the flanges 74 and 76 on the end cap 24.

The end cap 24 is then moved downwardly so that the flanges 68 and 70 on the hook portion 22 are received in the opening 90. Flat upper side surfaces 94 and 96 (FIGS. 5 and 7) on the hook portion flanges 68 and 70 are disposed in abutting engagement with a flat circular inner side surface 98 (FIG. 9) disposed on the end cap 24. A plurality of retainer or positioning walls 102, 104, 106 and 108 (FIGS. 8-10) engage the flanges 68 and 70 on the hook portion 22 to hold the end cap 24 in axial alignment with the hook portion 22.

The end cap 24 is then rotated through 90° relative to the hook portion 22. After the end cap has been rotated through 90°, a stop surface 114 (FIG. 9) formed in the end cap 24 abuttingly engages one of the flanges 68 and 70 on the hook portion 22. The stop surface 114 blocks further rotation of the end cap 24 relative to the hook portion 22.

When the end cap 24 has been rotated through 90° relative to the hook portion 22, one of the hook portion flanges 68 and 70 engage the stop surface 114. The flat upper side surfaces 94 and 96 (FIG. 5) on the hook portion flanges 68 and 70 are disposed in abutting engagement with the flat annular end surface 98 on a base portion 122 (FIG. 10) of the end cap 24. The flat under or lower (as viewed in FIGS. 5 and 6) side surface 82 of the hook flange 70 will be disposed in abutting engagement with the flat inner side surface 86 (FIGS. 8 and 10) on the end cap 24. Similarly, the flat lower side surface 80 (FIG. 5) on the hook flange 68 will be disposed in abutting engagement with an inner side surface of the end cap flange 76 (FIGS. 8 and 9).

Abutting engagement between the hook portion flanges 68 and 70 and end cap flanges 74 and 76 block axial movement of the end cap 24 relative to the hook portion 22. The inner side surfaces on the end cap flanges 74 and 76 extend parallel to the annular end surface 98 of the base 122. For example, the inner side surface 86 (FIG. 10) on the flange 74 is parallel to the end surface 98 of the base 122. A corresponding surface on the end cap flange 76 (FIG. 9) is also parallel to the base surface 98 on the end cap.

Figure 5:
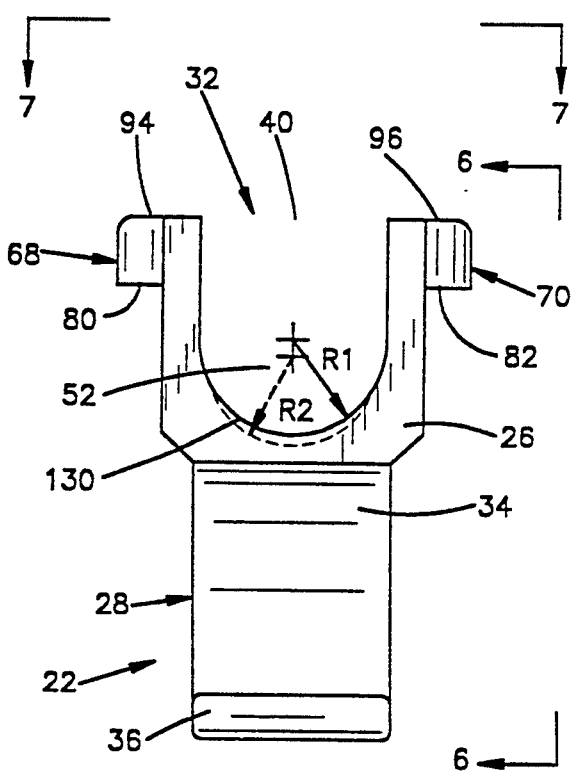
FIG. 5 is a front elevational view of the hook portion of the top-entry hook assembly of FIG. 1 and illustrating the relationship between a pair of connector flanges and an open ended recess in a body portion of the hook assembly.
Figure 6:
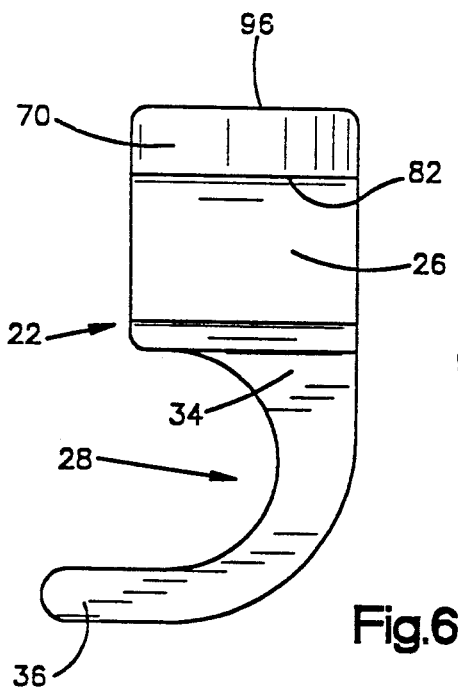
FIG. 6 is a side elevational view, taken generally along the line 6—6 of FIG. 5, further illustrating the construction of the hook portion.

Similarly, the upper and lower side surfaces on the hook portion flanges 68 and 70 extend parallel to each other (FIG. 5). Thus, the lower surfaces 80 and 82 extend parallel to the upper surfaces 94 and 96 of the flanges 68 and 70. Therefore, the flanges 68 and 70 on the hook portion 22 and the flanges 74 and 76 (FIGS. 8 and 9) on the end cap 24 cooperate with each other in such a manner as to permit rotational movement of the end cap relative to the hook portion.

The clamp member or set screw 60 is received in a threaded opening 124 (FIG. 10) formed in the center of the base 122 of the end cap 24. The set screw or clamp member 24 has a central axis 62 which extends perpendicular to and intersects the central axis 58 (FIG. 4) of the rod 48 when the rod 48 is disposed in the open ended recess 32 (FIG. 3) and the end cap 20 is connected with the hook portion 22.

When the set screw 60 is tightened or turned in the threaded opening 124, a leading end surface 126 (FIG. 10) on the set screw moves into abutting engagement with the rod 48 to press the rod against the arcuate bottom portion (FIG. 5) of the open ended recess 32. The force applied against the rod 48 by the set screw 60 presses the flanges 74 and 76 (FIG. 9) on the end cap 24 firmly against the flanges 68 and 70 (FIG. 5) on the hook portion 22 to hold the end cap against rotation relative to the hook portion.

Figure 18:
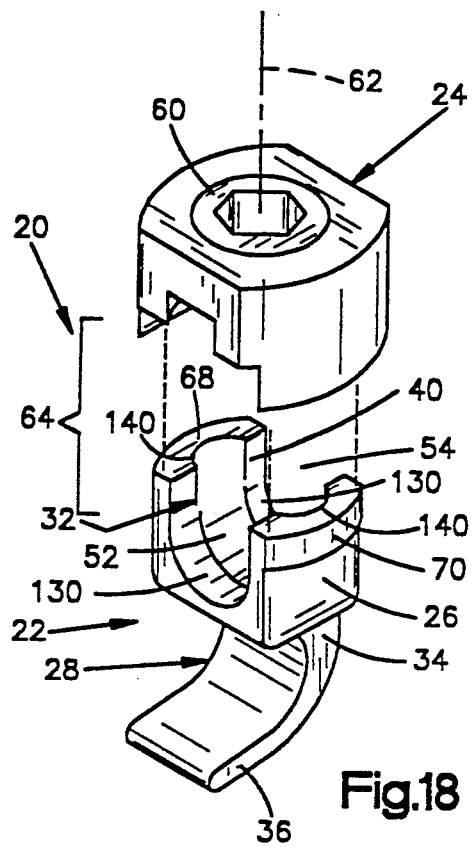
FIG. 18 is an exploded illustration, generally similar to FIG. 1, of a hook assembly of a fourth embodiment.
Figure 19:
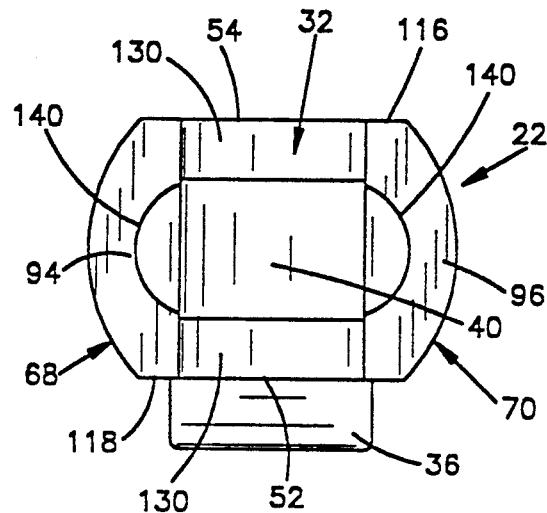
FIG. 19 is a top plan view of the hook portion of FIG. 18 illustrating the configuration of a side opening of the top-entry hook assembly.

If the rod 48 has a relatively small cross section the recess 32 (FIGS. 18 and 19) of the hook portion 22 includes vertical slots 140 in the sides of the upper side opening 40. The set screw 60 extends into the vertical slots 140 when the end cap 24 is connected with the hook portion 22.

Hook Assembly—Linear Cam Connector

In the embodiment of the invention illustrated in FIGS. 1-10, the end cap 24 is connected with the hook portion 22 by a bayonet connector 64. In the embodiment of the invention illustrated in FIGS. 11-14, the end cap and hook portion are interconnected by linear flange surfaces. Since the embodiment of the invention illustrated in FIGS. 11-14 is generally similar to the embodiment of the invention illustrated in FIGS. 1-10, similar numerals will be utilized to designate similar components, the suffix letter "a" being associated with the numerals of FIGS. 11-14 to avoid confusion.

The hook portion 22a of this embodiment of the top-entry hook assembly has a pair of rectangular flanges 68a and 70a (FIGS. 11 and 12). The flanges 68a and 70a extend parallel to each other and have a generally uniform cross section throughout their length. The flanges 68a and 70a are disposed at the upper end of a generally rectangular body 26a. A hook 28a is integrally formed with and extends downwardly from the body 26a and has a shank portion 34a and a free end or blade portion 36a.

An open ended recess 32a is formed in the body 26a of the hook portion 22a. The open ended recess 32a has an open upper side 40a, a generally U-shaped end opening 52a and a second end opening corresponding to the end opening 54 (FIG. 1) of the hook portion 22.

The end cap 24a (FIGS. 13 and 14) has a pair of linear flanges 74a and 76a which extend downwardly from a base portion 122a of the end cap. The base portion 122a has a flat rectangular lower side surface 98a. The side surface 98a of the base 122a engages rectangular upper side surfaces 94a and 96a (FIG. 11) on the hook portion flanges 68a and 70a.

The lower side surface 98a of the end cap base 122a is skewed downwardly slightly. Therefore, the distance between the lower side surface 98a and rectangular upper side surfaces of the end cap flanges 74a and 76a decreases along the length of the linear flanges. When the end cap 24a is moved along a linear path onto the hook portion 22a, the upper side surface 98a forms a cam which presses against the upper side surfaces 94a and 96a (FIG. 11) of the hook portion flanges 68a and 70a to grip the hook portion flanges with the flanges 74a and 76a on the end cap 24a. This camming feature is optional and could be eliminated.

Once the end cap 24a has been positioned on the hook portion 22a, a clamp member or set screw 60a is rotated to apply force against the rod disposed in the open ended recess 32a to press the rod against the bottom of the recess. In addition, the force applied against the rod by the set screw 60a results in the end cap flanges 74a and 76a being pulled upwardly against the hook portion flanges 68a and 70a to hold the end cap against movement relative to the hook portion 22a. The set screw 60a is disposed at the center of the end cap 24a.

Hook Assembly—Threaded Connector

In the embodiments of the invention illustrated in FIGS. 1-10 and 11-14 flanges on the end caps cooperate with flanges on the hook portions to interconnect the end caps and hook portions. In the embodiment of the invention illustrated in FIGS. 16-17, a threaded connection is provided between the end cap and hook portion. Since the embodiment of the invention illustrated in FIGS. 15-17 is generally similar to the embodiment of the invention illustrated in FIGS. 1-10, similar numerals will be utilized to designate similar components, the suffix letter "b" being added to the numerals of FIGS. 15-17 to avoid confusion.

The top entry hook assembly of FIGS. 15-17 includes a hook portion 22b (FIGS. 15 and 16) having a generally rectangular body 26b with a hook 28b extending downwardly from the body. The hook 28b has a shank 34b with a free end or blade portion 36b.

The body 26b of the hook portion 22b includes an open ended recess 32b (FIG. 15). The open ended recess 32b has an open upper side 40b. In addition, the recess has an open end 52b and an open end opposite from the end 52b and corresponding to the open end 54 of the recess 32 in the hook portion 22 of FIG. 1. A rod 48 can be inserted through the open upper side 40b of the recess 32b.

In accordance with a feature of this embodiment of the invention, an external thread convolution 132 is formed on the upper end of the body 26b. The end cap 24b (FIG. 17) has an internal thread convolution 134 which is engageable with the external thread convolution 132 to interconnect the end cap and the hook portion 22b.

Although the engagement of the internal threads on the end cap 24b with the external threads 132 on the body 26b will interconnect the end cap and body, there will be a clearance between the rod 48 and the end cap. Therefore, a clamp member or set screw 60b is provided in the center of the end cap 24b to clamp the rod securely in position relative to the hook 22b. When the set screw 60b is rotated to move into engagement with the rod, force is transmitted through the set screw to the end cap 24b. This force is transmitted to the threads 132 and 134 to hold them against relative rotation and to securely clamp the rod in place in the recess 32b.

Hook Assembly—Internal Cap Connector r In the embodiment of the invention illustrated in FIGS. 1-10, the end cap 24 is external to the recess 32 in the hook portion 22. In the embodiment of the invention illustrated in FIGS. 20-22, the end cap is internally connected to the hook portion. Since the embodiment of the invention illustrated in FIGS. 20-22 is generally similar to the embodiment of the invention illustrated in FIGS. 1-10, similar numerals will be utilized to designate similar components, the suffix letter "c" being associated with the numerals of FIGS. 20-22 to avoid confusion.

Figure 20:
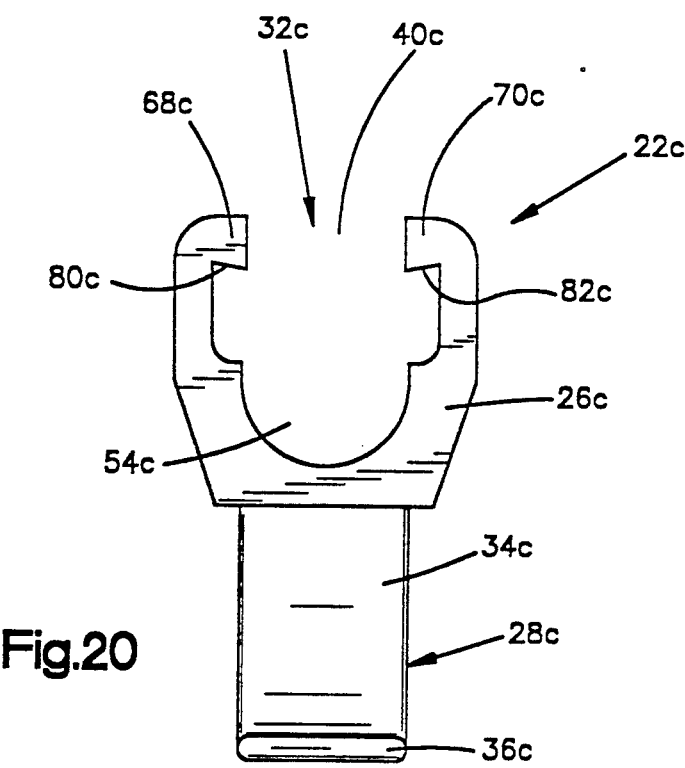
FIG. 20 is a front elevational view, generally similar to FIG. 5, of a hook portion of a fifth embodiment of the top-entry assembly.
Figure 25:
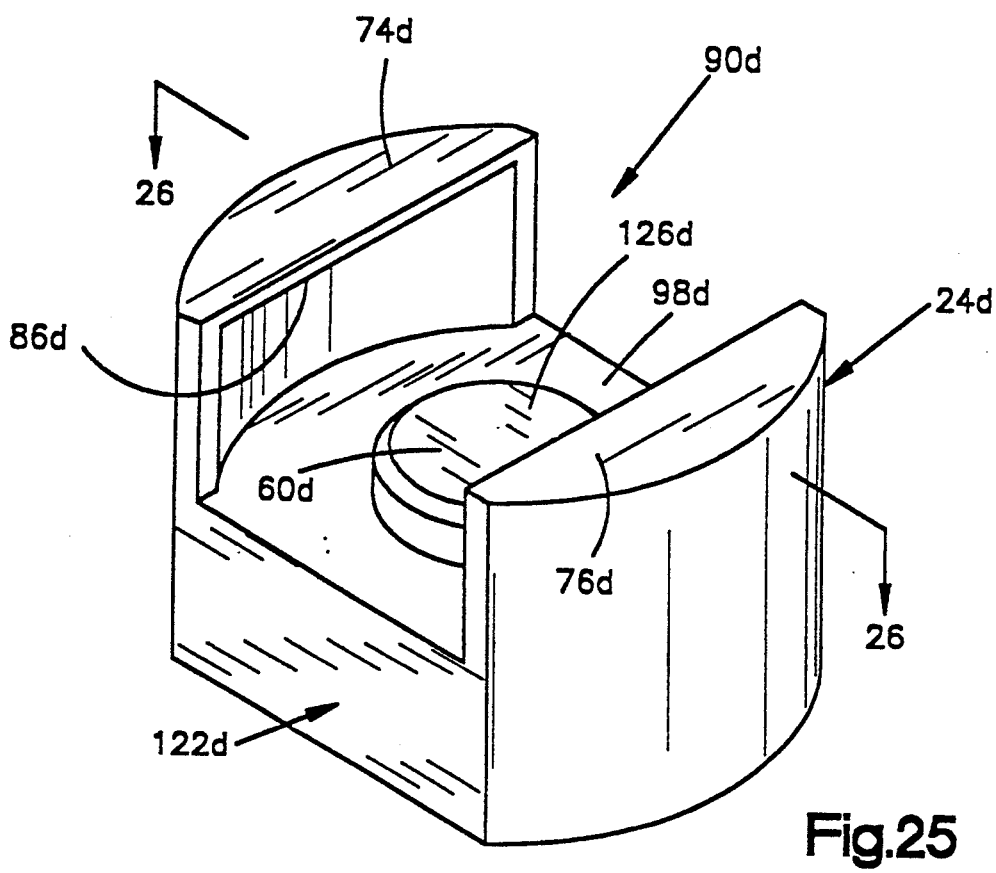
FIG. 25 is a pictorial illustration, generally similar to FIG. 8, of an end cap which is connected with the hook portion of FIG. 23, the lower side of the end cap facing upwardly to expose a pair of connector flanges.
Figure 26:
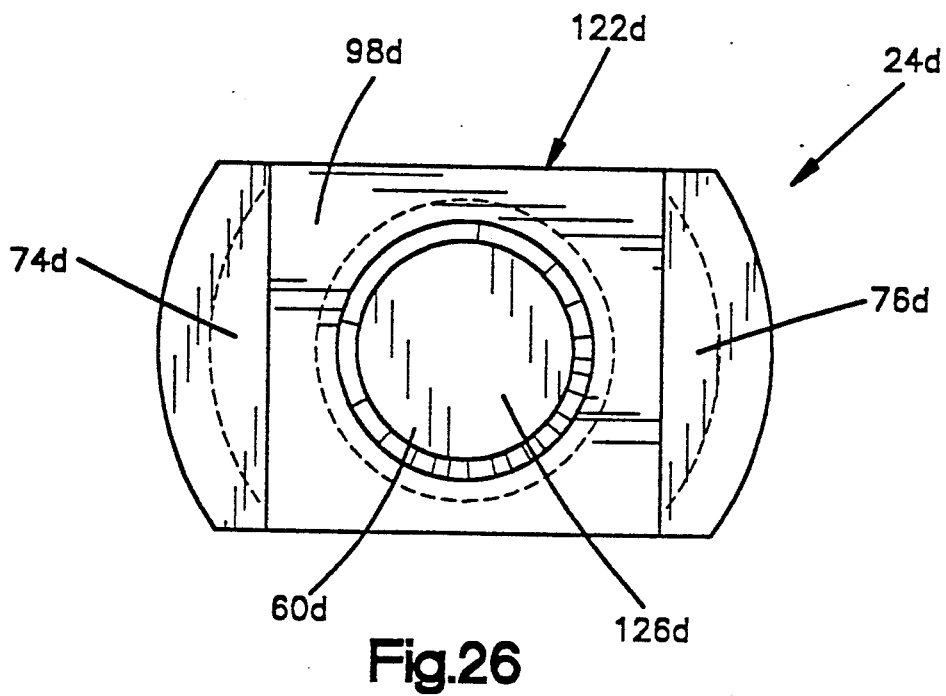
FIG. 26 is a bottom plan view taken generally along the line 26—26 of FIG. 25.

The hook portion 22c of this embodiment of the top-entry hook assembly has a pair of flanges 68c and 70c (FIGS. 20 and 22). The flanges 68c and 70c extend parallel to each other. The flanges 68c and 70c are disposed at the upper end of a generally rectangular body 26c. A hook 28c is integrally formed with and extends downwardly from the body 26c and has a shank portion 34c and a free end or blade portion 36c.

An open ended recess 32c is formed in the body 26c of the hook portion 22c. The open ended recess 32c has an open upper side 40c, an end opening 52c and a second end opening corresponding to the end opening 54 (FIG. 1) of the hook portion 22.

The end cap 24c (FIG. 21) has a pair of linear flanges 74c and 76c which extend outwardly from a base portion 122c of the end cap. When the end cap 24c is moved along a linear path onto the hook portion 22c, upper side surface 98c of flanges 74c and 76c engage lower side surfaces 80c and 82c of flanges 68c and 70c (FIG. 22).

Once the end cap 24c has been positioned on the hook portion 22c, a clamp member or set screw 60c is rotated to apply force against the rod disposed in the open ended recess 32c to press the rod against the bottom of the recess. In addition, the force applied against the rod by the set screw 60c results in the end cap flanges 74c and 76c being pulled upwardly against the hook portion flanges 68c and 70c to hold the end cap against movement relative to the hook portion 22c. The set screw 60c is disposed at the center of the end cap 24c. A lock nut 144 threadably engages the set screw 60c to clamp the flanges 68c and 70c of the body portion 26c between the lock nut and the flanges 74c and 76c of the end cap 24c to further hold the end cap against movement relative to the hook portion 22c.

As shown in FIGS. 21 and 22 the lower surface of the base portion 122c is concave to fit the rod. This concave surface also enables the cap to easily slide along the rod to easily engage into the hook.

Hook Assembly—Alternate Bayonet Connector

In the embodiment of the invention illustrated in FIGS. 1-10, the end cap 24 includes retainer walls 102, 104, 106 and 108. In the embodiment of the invention illustrated in FIGS. 23-26, the end cap does not include retainer walls. Since the embodiment of the invention illustrated in FIGS. 23-26 is generally similar to the embodiment of the invention illustrated in FIGS. 1-10, similar numerals will be utilized to designate similar components, the suffix letter "d" being associated with the numerals of FIGS. 23-26 to avoid confusion.

The body 26d (FIGS. 23-24) of the hook portion 22d has an open ended recess 32d which extends through the body and is open at opposite ends of the body to receive a rod or longitudinal member. The hook 28d includes a shank portion 34d and free end or blade portion 36d which are engageable with an element of a spinal column to interconnect the spinal column and a rod extending through the open ended recess 32d.

In accordance with one of the features of the present invention, the end cap 24d (FIGS. 25-26) is removable from the hook portion 22d. When the end cap 24d is removed from the hook portion 22d, a rectangular upper side opening 40d (FIG. 23) to the recess 32d is exposed. A rod or other longitudinal member can be readily inserted through the upper side opening 40d into the recess 32d. When the rod has been positioned in the recess 32d, the rod extends through a generally U-shaped end openings 52d and a second end opening corresponding to the end opening 54 (FIG. 1) of the hook portion 22.

Once the rod has been placed in the open ended recess 32d, the end cap 24d is connected with the hook portion 22d. The end cap 24d blocks the upper side opening 40d of the recess 32d while enabling the rod to extend through the end openings of the recess 32d. Once the end cap 24d has been connected with the hook portion 22d, a clamp member or set screw 60d (FIGS. 25 and 26) is tightened to interconnect the rod and hook assembly.

The clamp member or set screw 60d is located at the center of the end cap 24d. The set screw 60d presses the rod against the bottom of the recess 32d to clamp the rod against movement relative to the hook assembly 20d. In addition to pressing the rod against the bottom of the recess 32d, the set screw 60d applies an upwardly directed force against the end cap 24d to retain the end cap against disengagement from the hook portion 22d.

The body 26d (FIGS. 23 and 24) of the hook portion 22d includes a pair of flanges 68d and 70d disposed at the upper end of the body. When the end cap 24d is connected with the hook portion 22d, the flanges 68d and 70d are enclosed by the end cap and engage flanges 74d and 76d (FIGS. 25 and 26) formed on the end cap 24d. When the end cap 24d is connected with the hook portion 22d, the flanges 74d and 76d on the end cap 24d engage in a groove 150 (FIGS. 23 and 24) in the body 26d. The groove 150 extends entirely around the body 26d.

When the end cap 24d is connected with the hook portion 22d, the flat lower side surface 80d on the hook flange 68d (FIG. 23) abuttingly engages a flat inner side surface 86d (FIG. 25) on the end cap flange 74d. Similarly, the flat lower side surface 82d (FIG. 23) on the hook flange 70d abuttingly engages a flat inner side surface (not shown) on the end cap flange 76d. Abutting engagement between the flanges 68d and 70d on the hook portion 22d and the flanges 74d and 76d on the end cap 24d hold the end cap on the hook portion 22d. The end cap 24d extends across the open upper side 40d of the recess 32d to close the recess.

After the rod has been inserted through the open upper side 40d of the recess 32d, the end cap 24d is connected with the hook portion 22d. This is accomplished by positioning the end cap 24d in axial alignment with the hook portion 22d with the flanges 74d and 76d facing downwardly toward the flanges 68d and 70d on the hook portion 22d. A transverse opening 90d (FIG. 25) between the flanges 74d and 76d on the end cap 24d is aligned with the flanges 68d and 70d (FIG. 23) on the upper end of the hook portion 22d. At this time, the flanges 68d and 70d on the hook portion 22d are offset by 90° from the flanges 74d and 76d on the end cap 24d.

The end cap 24d is then moved downwardly so that the flanges 68d and 70d on the hook portion 22d are received in the opening 90d. Flat upper side surfaces 94d and 96d (FIG. 23) on the hook portion flanges 68d and 70d are disposed in abutting engagement with a flat inner side surface 98d (FIGS. 25 and 26) disposed on the end cap 24d.

The end cap 24d is then rotated through 90° relative to the hook portion 22d. When the end cap 24d has been rotated through 90° relative to the hook portion 22d, the end cap flanges 74d and 76d engage in the groove 150. The flat upper side surfaces 94d and 96d (FIG. 23) on the hook portion flanges 68d and 70d are disposed in abutting engagement with the flat end surface 98d on a base portion 122d (FIG. 25) of the end cap 24d. The flat under or lower (as viewed in FIG. 23) side surface 82d of the hook flange 70d will be disposed in abutting engagement with the flat inner side surface 86d (FIG. 25) on the end cap 24d. Similarly, the flat lower side surface 80 (FIG. 23) on the hook flange 68d will be disposed in abutting engagement with an inner side surface of the end cap flange 76d.

When the set screw 60d is tightened, a leading end surface 126d (FIGS. 25 and 26) on the set screw moves into abutting engagement with the rod to press the rod against the bottom portion of the open ended recess 32d (FIG. 23). The force applied against the rod by the set screw 60d presses the flanges 74d and 76d (FIG. 25) on the end cap 24d firmly against the flanges 68d and 70d (FIG. 23) on the hook portion 22d to hold the end cap against rotation relative to the hook portion. While the hook of FIG. 23 has been described above for use with the cap of FIG. 25, the hook of FIG. 23 could also be used with the cap of FIG. 8 if the parts are properly dimensioned.

Conclusion

In view of the foregoing description, it is apparent that the present invention provides an apparatus for use in retaining a longitudinally extending member 48 in position relative to a spinal column 44. The apparatus includes a top-entry hook assembly 20 which can be positioned relative to the longitudinal member or rod 48 without moving the hook assembly 20 along the rod and/or moving another article, such as a locknut or sleeve, along the rod. The hook assembly 20 includes a body 26 having an open ended recess 32 which extends through the body and is open at both ends 52 and 54 and along one side 40 to enable the rod 48 to be moved into the recess. A hook 28 extends from a side of the body 26 opposite from the side opening 40 through which the rod is inserted into the recess 32. The hook 28 is engageable with a spinal column 44. Once the hook 28 has engaged the spinal column 44 and the rod 48 inserted into the recess 32, an end cap 24 is connected with the body 26 to block the side opening 40 through which the rod 48 was moved into the recess. A clamp member 60 is disposed in the center of the end cap 24 to clamp the rod 48 against the bottom of the recess 32 in the body 26.

One embodiment of the end cap includes a bayonet connector 64 which is readily engaged under adverse conditions which may be encountered during an implant procedure. The bayonet connector 64 includes flanges 68 and 70 disposed on an upper end of the body 26 and mating flanges 74 and 76 disposed on the end cap 24. When the end cap 24 and body 26 are to be interconnected, the end cap is telescoped over the flanges 68 and 70 on the body 26 and then rotated to engage the flanges on the body with the flanges 74 and 76 on the end cap.

Another connector (FIGS. 11-14) for interconnecting an end cap 24a and body 26a includes linear flanges 68a and 70a on the body which engage linear flanges 74a and 76a on the end cap. The linear flanges on either the body 26a or the end cap 24a have cam surfaces 98a which interact with flange surfaces to hold the end cap 24a in place. In another embodiment of the top-entry hook assembly (FIGS. 15-17), the body 26b is provided with an external thread convolution 132 which is engaged by an internal thread convolution 134 on the end cap 24b.

In another embodiment of the top-entry hook assembly (FIGS. 20-22) the end cap 24c is internal to the recess 32c. Linear flanges 74c and 76c on the end cap 24c engage linear flanges 68c and 70c on the body 26c. A lock nut 144 and set screw 60c hold the end cap 24c in position relative to the body 26c.

In another embodiment of the top-entry hook assembly (FIGS. 23-26) the end cap 24d is provided with an alternative bayonet connector. Flanges 68d and 70d disposed on an upper end of the body 26d mate with flanges 74d and 76d disposed on the end cap 24d. The flanges 74d and 76d on the end cap 24d extend into a groove 150 formed in the body 26d just below the flanges 68d and 70d on the body. When the end cap 24d and the body 26d are to be interconnected, the end cap 24d is telescoped over the flanges 68d and 70d on the body and rotated to engage flanges 68d and 70d on the body with the flanges 74d and 76d on the end cap.

It should be clear that in all embodiments the recess which receives the rod has the configuration shown in FIG. 5 which is described in detail in U.S. Pat. No. 5,024,213.

It should be clear from the above that modifications and changes may be made to the present invention. For example, the connector designs described above could be used on a screw or post to attach a rod to the screw or post. In effect, the connector designs can be used with parts other than the hooks shown in the drawings. It is intended to cover all such modifications and changes within the scope of the appended claims.

Having described specific preferred embodiments of the invention, the following is claimed:

1. An apparatus for use in retaining a longitudinally extending member in position relative to a spinal column, said apparatus comprising a body having an open ended recess which extends through the body and is open along one side to enable the longitudinally extending member to be moved into the recess, said recess having a side opening, a first end opening formed in a first side of the body and intersecting the side opening, and a second end opening formed in a second side of the body opposite from the first side and intersecting the side opening to enable the longitudinally extending member to be moved into the recess through the side opening and to extend from the first and second sides of said body through the first and second end openings, said body including first and second flanges disposed on opposite sides of said side opening, a connector element extending from a side of said body opposite from the side opening and connectable with the spinal column to connect said body with the spinal column, an end cap movable between a disengaged position spaced from said body and an engaged position at least partially enclosing said body and extending across the side opening in said body, said end cap including a base, a first linear cam surface connected with and disposed adjacent a first side of said base, and a second linear cam surface connected with and disposed adjacent to a second side of said base, said first flange being engageable with said first cam surface and said second flange being engageable with said second cam surface upon movement of said end cap relative to said body along a linear path, said first and second cam surfaces being disposed in a plane which extends at an acute angle to a central axis of the recess and which extends through the first and second end openings of the recess to enable said first and second cam surfaces to move said end cap toward the central axis of the recess upon movement of said end cap along the linear path, and a clamp member mounted on said end cap, said clamp member being movable relative to said end cap when said end cap is in the engaged position to clamp a longitudinally extending member disposed in the recess against said body and to press said first and second cam surfaces against said first and second flanges to hold said end cap against movement from the engaged position to a disengaged position.

2. An apparatus as set forth in claim 1 wherein said connector element is a hook which extends from a side of said body opposite from the side opening and which is engageable with the spinal column, said hook having a shank portion connected with said body and a free end portion extending from said shank portion in the direction of a plane extending through the second side of said body to enable said hook to engage an element of the spinal column when the longitudinally extending member is disposed in the recess.

3. An apparatus as set forth in claim 1 wherein said clamp member is a single set screw which is rotatable relative to said end cap to clamp the longitudinally extending member and said body together when the longitudinally extending member is in the recess.

4. An apparatus for use in retaining a longitudinally extending member in position relative to a spinal column, said apparatus comprising a body having an open ended recess which extends through the body and is open along one side to enable the longitudinally extending member to be moved into the recess, said recess having a side opening, a first end opening formed in a first side of the body and intersecting the side opening, and a second end opening formed in a second side of the body opposite from the first side and intersecting the side opening to enable the longitudinally extending member to be moved into the recess through the side opening and to extend from the first and second sides of said body through the first and second end openings, said body including first and second flanges disposed on opposite sides of said side opening, a connector element extending from a side of said body opposite from the side opening and connectable with the spinal column to connect said body with the spinal column, an end cap movable between a disengaged position spaced from said body and an engaged position at least partially enclosing said body and extending across the side opening in said body, said end cap including a first surface lying in a first plane, and a second surface lying in a second plane, said second plane extending at an acute angle to said first plane and extending at an acute angle to a central axis of the recess, said first and second surfaces being engageable with surfaces on said body to grip said body between said first and second surfaces on said end cap, and a clamp member mounted on said end cap, said clamp member being movable relative to said end cap when said end cap is in the engaged position to clamp a longitudinally extending member disposed in the recess against said body.

5. An apparatus for use in retaining a longitudinally extending member in position relative to a spinal column, said apparatus comprising a body having an open ended recess which extends through the body and is open along one side to enable the longitudinally extending member to be moved into the recess, said recess having a side opening, a first end opening formed in a first side of the body and intersecting the side opening, and a second end opening formed in a second side of the body opposite from the first side and intersecting the side opening to enable the longitudinally extending member to be moved into the recess through the side opening and to extend from the first and second sides of said body through the first and second end openings, said body including first and second flanges disposed on opposite sides of said side opening, a connector element extending from a side of said body opposite from the side opening and connectable with the spinal column to connect said body with the spinal column, an end cap movable between a disengaged position spaced from said body and an engaged position at least partially enclosing said body and extending across the side opening in said body, said end cap including a first surface having first and second end portions and a second surface having first and second end portions, said first end portion of said first surface being spaced from said first end portion of said second surface by a first distance, said second end portion of said first surface being spaced from said second end portion of said second surface by a second distance, the second distance being less than the first distance, said first and second surfaces being engageable with surfaces on said body to grip said body, and a clamp member mounted on said end cap, said clamp member being movable relative to said end cap when said end cap is in the engaged position to clamp a longitudinally extending member disposed in the recess against said body.

* * * * *